(12) United States Patent
Groger et al.

(10) Patent No.: US 6,277,651 B1
(45) Date of Patent: Aug. 21, 2001

(54) DIODE LASER ELECTROCHEMICAL SENSOR FOR DETECTING CHEMICAL AND BIOLOGICAL ANALYTES

(75) Inventors: Howard P. Groger, Gainesville, FL (US); Myron T. Coolbaugh, Christiansburg, VA (US); K. Peter Lo, Blacksburg, VA (US); Russell J. Churchill, Radford, VA (US)

(73) Assignees: Calspan SRL Corporation, Buffalo, NY (US); a part interest; American Research Corporation of Virginia, Radford, VA (US); a part interest ( * ) Notice: Subject to any disclaimer, the term of this patent is extended or adjusted under 35 U.S.C. 154(b) by 0 days.

(21) Appl. No.: 09/111,735

(22) Filed: Jul. 9, 1998

(51) Int. Cl.⁷ .................................................. G01N 33/543

(52) U.S. Cl. .................. 436/518; 436/172; 436/164; 257/253; 257/414; 372/44; 372/43; 422/82.05; 422/82.08; 422/82.07; 422/82.09; 422/82.11; 356/318

(58) Field of Search .................................. 257/253, 414; 372/44, 43; 436/172, 164, 518; 422/82.05, 82.08, 82.07, 82.09, 82.11; 356/318

(56) References Cited

U.S. PATENT DOCUMENTS

| | | | |
|---|---|---|---|
| 4,169,676 | 10/1979 | Kaiser | 356/39 |
| 4,819,036 | 4/1989 | Kuroda et al. | 357/4 |
| 4,844,613 | 7/1989 | Batchelder et al. | 356/318 |

(List continued on next page.)

OTHER PUBLICATIONS

Sambrook et al. (1989). Molecular Cloning, A Laboratory Manual. 2nd Edition. Cold Spring Harbor Laboratory Press. p. 1.103.*

Zhengfang et al. (1993). Fiber–optic pH sensor based on evanescent wave absorption spectroscopy. Anal. Chem. 65:2335–2338.*

Wu et al. (1994). Conducting polyaniline filaments in a mesoporous channel host. Science. 264:1757–1759.*

Jung et al. (1996). Polymeric mercaptosilane–modified platinum electrodes for elimination of interfeants in glucose boisensors. Anal. Chem. 68:591–596.*

Johnson et al. (1990). Liquid chromatography with pulsed electrochemical detection. Anal. Chem. 62(10):589A–597A.*

Groger et al. (1996). Polymeric sensor materials for GB and DMMP detection. in Proc. EDRC Sci. Conf. Chem. Biol. Def. Res. (Ed. Berg). Meeting date 1995, pp. 37–43.*

Lo et al. (1998). Novel surface–sensitive diode lasers for chemical detection. Proc. SPIE–Int. Soc. Opt. Eng. 3547 (Semiconductor Lasers III):394–401.*

Dai et al., "In GaAs/GaAs single quantum well lasers with monolithically integrated multilayer wave guides for surface–emitted sum–frequency generation", Canadian Journal of Physics, 1992, vol. 70, pp. 921–927.

Wu et al., "Large wavelength shifts in thin p–clad In GaAs QW lasers", University of Florida, Dept. of Electrical Engineering, Gainesville, Florida, pp. 1–3.

Primary Examiner—Christopher L. Chin
Assistant Examiner—Minh-Quan K. Pham
(74) Attorney, Agent, or Firm—James Creighton Wray; Meera P. Narasimhan

(57) ABSTRACT

The present sensor allows the user of any diode laser structure to be employed to provide sensitive chemical and biological detector. A diode laser electrochemical sensor is described in U.S. Pat. No. 5,591,407 "Laser Diode Sensor". The present invention surpasses the capabilities of those sensors by measuring changes in the output power, output spectral characteristics or output signal auto-correlation function to detect the presence of chemical or biological films within the sensitive region.

5 Claims, 1 Drawing Sheet

U.S. PATENT DOCUMENTS

| | | | |
|---|---|---|---|
| 4,880,752 | 11/1989 | Keck et al. | 435/7 |
| 4,894,833 * | 1/1990 | Carlin | 372/44 |
| 5,047,213 | 9/1991 | Finlan et al. | 422/82.11 |
| 5,107,316 | 4/1992 | Jelley et al. | 357/25 |
| 5,109,386 * | 4/1992 | Bradley | 372/32 |
| 5,132,097 | 7/1992 | Van Deusen et al. | 422/82.09 |
| 5,177,758 | 1/1993 | Oka et al. | 372/50 |
| 5,194,393 | 3/1993 | Hugl et al. | 436/525 |
| 5,208,878 * | 5/1993 | Thulke | 385/14 |
| 5,212,099 | 5/1993 | Marcus | 436/172 |
| 5,268,145 | 12/1993 | Namba et al. | 422/57 |
| 5,298,428 | 3/1994 | O'Rourke et al. | 436/171 |
| 5,298,741 | 3/1994 | Walt et al. | 250/227.23 |
| 5,299,141 | 3/1994 | Hungerford et al. | 364/510 |
| 5,308,771 | 5/1994 | Zhou et al. | 436/39 |
| 5,317,897 | 6/1994 | Jelley et al. | 73/31.06 |
| 5,403,451 * | 4/1995 | Riviello et al. | 204/153.1 |
| 5,439,647 | 8/1995 | Saini | 422/82.11 |
| 5,491,712 * | 2/1996 | Lin et al. | 372/50 |
| 5,492,840 | 2/1996 | Malmqvist et al. | 436/518 |
| 5,506,420 * | 4/1996 | Kossovsky et al. | 257/40 |
| 5,585,646 * | 12/1996 | Kossovsky et al. | 257/40 |
| 5,591,407 * | 1/1997 | Groger et al. | 422/82.05 |
| 5,665,582 * | 9/1997 | Kausch et al. | 435/181 |
| 5,766,956 * | 6/1998 | Groger et al. | 436/164 |
| 5,774,603 * | 6/1998 | Moore et al. | 385/12 |
| 5,804,453 * | 9/1998 | Chen | 436/518 |
| 5,925,354 * | 7/1999 | Fuller et al. | 424/184.1 |
| 5,981,203 * | 11/1999 | Meyerhoff et al. | 435/7.92 |

* cited by examiner

DIODE LASER ELECTROCHEMICAL SENSOR FOR DETECTING CHEMICAL AND BIOLOGICAL ANALYTES

BACKGROUND OF THE INVENTION

U.S. Pat. No. 5,591,407 describes the use of specific surface sensitive diode laser structures in chemical and biological analysis. In as aspect of that patent the interaction between the laser sensor and the material being sensed is based on the absorption of the material within the effective laser cavity at the surface of the laser. In the present invention, any diode laser may be employed to provide a sensitive chemical or biological detector.

SUMMARY OF THE INVENTION

The finding by LARGENT (1996) Liquid Contact Luminescence, Dissertation, Electrical Engineering Department, University of Florida, Gainesville, Fla. that semiconductor laser wafer material could produce bright optical emission with a liquid contact provides the background to this invention.

The present sensor allows the use of any diode laser structure to be employed to provide a sensitive chemical and biological detector. A diode laser electrochemical sensor is described in U.S. Pat. No. 5,591,407 "Laser Diode Sensor." The present invention surpasses the capabilities of those sensors by measuring changes in the output power, output spectral characteristics or output signal auto-correlation function to detect the presence of chemical or biological films within the sensitive region.

A diode laser is on top of a substrate. A lasing structure is positioned on top of the substrate. A cap layer is positioned on top of the lasing structure. A segmented electrode is positioned on top of the cap layer. Gaps between the segments of the electrode act as chemical sensors. A sensitive coating is positioned on the cap layer between the segments of the electrode.

In preferred embodiments, passivation at the facets of the diode laser protects the edges from shorting on application of conductive layers. Passivation is accomplished by a layer of electron beam evaporated aluminum oxide. Deposition can be accomplished by laser ablation or magnetron sputtering.

In preferred embodiments, the electrodes and regions between the segmented electrodes are coated by a thin metal island layer. For example, an electron-beam evaporated gold island layer is deposited at thicknesses between 2 nm and 20 nm. Also, the coating containing gold metal islands between the segmented electrodes is modified using cross linked molecules such as (4-succinimidyloxycarbonyl-methyl-a-(2-pyridyldithio)toluene) (SMPT) (spacer arm 2.0 nm) or (m-Maleimidobenzoyl-N-hydrosuccinimide ester) (MBS) (spacer arm 0.99 nm). In this case, the diode laser is first brought into contact with Cleland's reagent (dithiothreitol) (DTT) in excess. Other dithiols include xylyl dithiol, phenyl dithiol, dithiodibenzoic acid, biphenyl dithiol, 1,4-di(4-thiophenylacetylnyl)-2-ethylbenzene (20ADT) and terphenyl dithiol. The laser coated with DTT is then exposed to SMPT or MBS conjugated to a protein of interest. Optimally, the gold coating in the gap region between the contact electrodes should be between 2 nm and 20 nm thick.

In preferred embodiments, a conductive polymer may be deposited in the gap region by electro-deposition or electro polymerization as described U.S. Pat. No. 5,403,451, titled "Method and Apparatus for Pulsed Electrochemical Detection Using Polymer Electroactive Electrodes" to Rivello et al. Poly(pyrrole), poly(thiophene), poly(aniline) or other conducting polymer may be used for this purpose.

A thin film may be used to isolate a sample for testing. In preferred embodiments, the thin film is a capture antibody layer, deposited over a thin oxide layer. The oxide between the contact electrodes is first modified with (3-mercaptopropyl trimethoxysilane) (MPTS). Subsequently, (3-maleimidoprorionic acid) (MPA) followed by 1-ethyl-3-(3-diethylamino propyl)carbodiimide hydrochloride are deposited on the gold layer after the manner suggested by JUNG and WILSON (1996) Polymeric Mercaptosilane-Modified Platinum Electrodes for Elimination of Interference in Glucose Biosensors, Anal. Chem. 68, pp. 591–596. Finally, a 5 microLiter sample of capture antibody solution (1 mg/ml in saline buffer) is brought into contact with the diode laser surface for 24 hours. Similarly, 3-gylcidoxypropyl trimethoxysilane (GPTS) may be deposited directly over the thin oxide layer. The capture antibody may be linked to the oxide layer via N-γ-maleimidobutyryloxy succinimidyl ester (GMBS).

In a preferred embodiment, the thin film in the region between the contact electrodes is deposited by first depositing a thin metal island gold layer (2 nm to 20 nm) and then the laser is allowed to come into contact for 24 hours with a 2% solution of thioctic acid in ethanol. Next, the surface of the diode laser is allowed to dry and then is immersed into a solution of 1% by weight 1-ethyl-3-(3-diethylamino propyl)carbodiimide in acetonitrile for 5 hrs. Finally, a 5 microLiter sample of capture antibody solution (1 mg/ml in saline buffer) is brought into contact with the diode laser surface for 24 hours. The interaction between the laser surface and the capture antibodies in the film is detected as a change in laser output. Changes in output power, output spectral characteristics or output signal auto-correlation function occur where chemical or biological antigens are brought into the vicinity of the surface of the diode laser. The diode laser may also be prepared by deposition of DTT on the laser surface. In a separate reaction, the capture antibody is coupled to SMPT or MBS. Then the DTT-coated laser is coated with antibody-coupled SMPT or MBS. This results in the immobilization of the antibody at the laser surface. Other thiols that may be used to couple the sense molecule to the diode laser surface include xylyl dithiol, phenyl dithiol, dithiodibenzoic acid, biphenyl dithiol, 1,4-di(4-thiophenylacetylnyl)-2-ethylbenzene (20ADT) and terphenyl dithiol. Similarly, the gold coating may be functionalized using isocyanide-based molecules.

In preferred embodiments, the sense film is an oligonucleotide sequence. The sense film is deposited on the diode laser surface using a hybridization solution containing standard saline citrate (SSC), N-lauroylsarcosine, sodium dodecyl sulfate (SDS) and a target deoxyribonucleic acid (DNA) sequence. An oligonucleotide sequence may be deposited at the surface of the diode laser by first coating the diode laser with a thin gold layer. The complimentary oligonucleotide sequence is synthesized with a sulfhydryl group to allow coupling to the laser surface.

A flow cell may be used to bring samples past the diode laser surface where the diode laser is fabricated onto a flow cell. Material flowing in the cell is brought to the surface of the diode laser in the region of the gap. In preferred embodiments, a thin film heater is built into the flow cell to allow denaturing sample DNA and immobilized DNA by heating at 95° C. for 5 minutes or so. The results of hybridization are detected as a change in the output power, output spectral characteristics or output signal autocorrelation function.

Chemical or biological detection is accomplished by monitoring optical output. For this purpose, one or more electrodes may be placed in gap between the segments of the electrode. Two or more additional electrodes may be used to modulate the potential in the gap region.

The modulating electrodes within the gap between the contact electrodes are pulsed in a manner described in JOHNSON and LACOURSE (1990) Liquid Chromatography With Pulsed Electrochemical Detection at Gold and Platinum Electrodes, Anal. Chem., 62 (10), pp. 589a–597a. The potential of one of the two electrodes within the gap region is increased from a starting point of −0.8V to a maximum potential of +0.8V within a short time frame and the output of the diode laser is monitored just after the potential increase. Subsequently, the applied potential of the diode laser gap electrodes from +0.8V to +0.2V is performed, after which time the output signal of the diode laser is monitored.

Where a flow cell is used for sampling, the voltage between gap electrode and contact electrode may be as high as the hydrolyzing voltage (−1.0 V in water or −2 V in organic solvents). The potential is applied according to a range of waveforms (step, triangular or sinusoid). The laser output is monitored as a change in the output power, output spectral characteristics or output signal auto-correlation function.

A preferred embodiment has a gap between the contact electrodes of about 60 microns long and the has a width of the contact electrodes of about 5 microns, and end facets of the diode laser have been passivated using an electron beam deposited alumina layer and the end facets are made of highly reflective using alternating gold and alumina layers and a 10 nm thick gold film has been evaporated in the region between the contact electrodes, that film being patterned by standard or electron beam lithography to produce a set of electrodes within the gap.

A diode laser sensor has a gap in the contact electrode. The gap is not more than 150 microns in length and not less than 2 microns. The laser exhibits a change in output power, output spectral characteristics or output signal autocorrelation function depending upon the presence of chemical or biological films within the sensitive region.

In preferred embodiments, a diode laser has electrodes fabricated within the gap region. One of said electrodes can be used to monitor the laser optical output and two or more electrodes can be used to modulate the potential in the gap region.

The facets of the diode laser are passivated using an electron beam evaporated aluminum oxide layer. The passivation is deposited by laser ablation or magnetron sputtering. Passivation at the facets is used to protect the edge of the diode laser from shorting on application of conductive layers.

In preferred embodiments, the interaction between the laser surface and the capture antibodies is detected as a change in laser output. Where the change is detected as a change in output power, output spectral characteristics or output signal autocorrelation function depending upon presence of chemical or biological antigens brought to the vicinity of the surface of the diode laser.

The thin gold coating between the contact electrodes is prepared using cross linked molecules, such as (4-succinimidyloxycarbonyl-methyl-a-(2-pyridyldithio) toluene (SMPT) (spacer arm 2.0 nm), to serve as a basis on which to immobilize the capture antibody or nucleic acid probes.

These and further and other objects and features of the invention are apparent in the disclosure, which includes the above and ongoing written specification, with the claims and the drawings.

BRIEF DESCRIPTION OF THE INVENTION

DETAILED DESCRIPTION OF THE PREFERRED EMBODIMENTS

Figure 1:
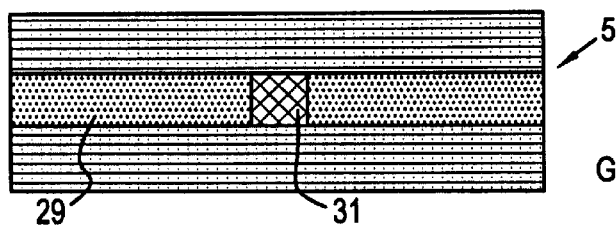
FIG. 1 is a top view of a laser with a gapped electrode.

In the present invention, a diode laser structure 5 is employed to provide a sensitive chemical or biological detector. In one preferred embodiment, the diode laser 5 is fabricated with a gap 31 between the surface electrodes. The top view of the diode laser 5 with a gapped electrode 29 is shown in FIG. 1. In the gap region 31 between the electrodes 29, semiconductor material is within a distance of the laser surface. If a laser 5 of that design is placed in an electrolyte, charge transfer may occur between ionic species in the electrolyte and the semiconductor surface.

Figure 2:
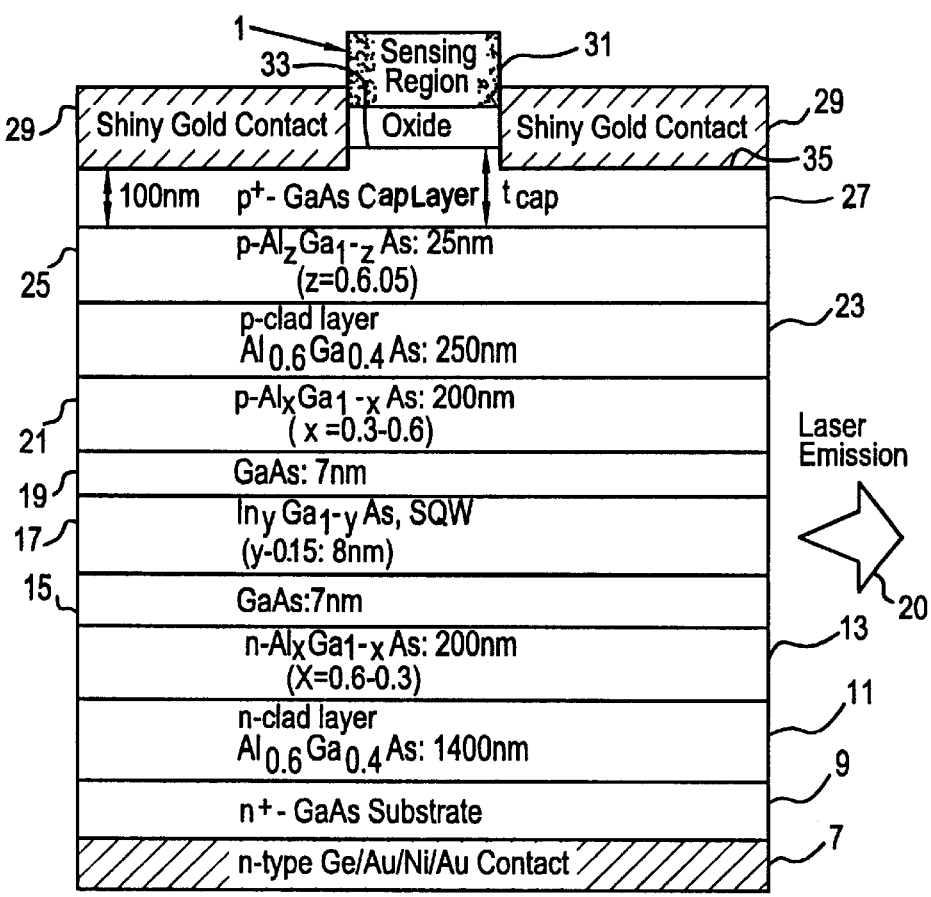
FIG. 2 is a side view of a laser showing the sensitive gap region.

A layer structure of the diode laser system 5 appears in FIG. 2 showing an unpumped region 33 of the laser 5 between the two shiny gold contacts 29 that serves as the sensing region 31 where the label is deposited. FIG. 2 also shows a pumped region 35 of the laser 5 protected by the shiny gold contacts 29 having little or no interaction with the environment. In a solution with little or no conductivity, the gap 31 between the shiny gold contacts 29 reduces the laser output at any injection current and increases the laser threshold current. The conducting ions in solution serve as a liquid contact that increases the laser output by reducing the effective length of the gap 31. In an aqueous electrolyte, hydrogen ions migrate toward the $p^+$ gallium arsenide (GaAs) cap layer 27 of the laser wafer. To allow current to flow in the cell, the hydrogen ions capture electrons from the $p^+$ cap layer 27 near the top surface in FIG. 2, thereby creating holes in the valence band. The holes are injected from the cap layer 27 toward the single quantum well (SQW) 17, shown in FIG. 2. The liquid electrolyte serves as an electrical contact to the laser wafer. Electrons are injected to the negative section of the substrate from the n-type germanium/gold/nickel contact 7 shown at the bottom of FIG. 2. The recombination of holes and electrons in the SQW 17 results in the emission of light 20.

The recombination rate for non-radiative emission ($R_{nr}$) and spontaneous emission ($R_{sp}$) with the gap may be related to the carrier density as $R_{nr}=ANV$ and $R_{sp}=BN^2V$, where A and B are the non-radiative and spontaneous recombination coefficients, N is the carrier density in the active region and V is the volume of the active region. The internal quantum efficiency, $\eta i$, of the material within the gap may be calculated from $\eta i\ I/e = R_{nr}+R_{sp}$ where I is the current (Amperes) and e is the charge of an electron. Since the volume may be taken as the width, w, times the length, l, times the depth, d, the equation may be presented as $\eta i J/(ed) = AN+BN^2$, where J is the current density. The current density in the semiconductor depends on the current density in the electrolyte. At an applied electric field, E, the current density, $J_{et}$, resulting from transfer of electrons from the semiconductor to the electrolyte, may be written as $J_{et}(E)=qk_{et}n_s(E)$ (A), where q is the elementary charge on an electron, $k_{et}$ is charge transfer rate constant between a charge carrier in the semiconductor and an outer-sphere redox species in the electrolyte, $n_s$ is the number of electrons at the semiconductor surface, A is the concentration of acceptors in the interfacial region. Work performed by LARGENT (1996) Liquid Contact Luminescence, Dissertation, Electrical Engineering Department, University of Florida, Gainesville, Fla. indicated a nonlinear dependence of the luminescence output amplitude on the concentration of acceptor materials in solution. For tetrabutylammonium perchlorate (TBAP) in propylene carbonate, the luminescence increased exponentially with increasing concentration of TBAP.

Figure 3:
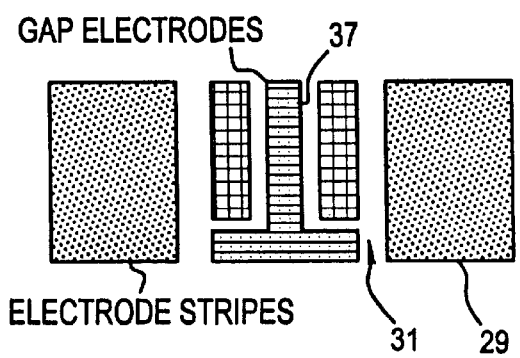
FIG. 3 is an expanded view of a laser gap region showing microelectrodes within the gap.

FIG. 3 shows the gap region 31 of the diode laser 5 with micro-electrodes 37 deposited within the gap. The gap micro-electrodes 37 are deposited using electron-beam evaporation or magnetron sputtering and are patterned using microlithographic techniques. Micro-electrode 37 thickness may be in the 20 nm to 40 nm range. All electrodes 37 at the laser surface are connected to bonding pads that are deposited on the substrate 9 using e-beam evaporation procedures. The applied voltage at each of the electrodes may be altered to provide an instrument response that optimizes the detection of changes in the electrochemical characteristics of the materials deposited at the laser surface. Since the sensitive area of the diode laser is 150 μm by 100 μm or less, it is necessary to confine sample flow to a restricted volume to ensure interaction between the probe and the detector. That may be achieved through the use of microfluidics.

While the invention has been described with reference to specific embodiments, modifications and variations of the invention may be constructed without departing from the scope of the invention, which is defined in the following claims.

We claim:

1. A method for chemical and biological sensing comprising providing a diode laser with a layered semiconducting structure, and a cap layer positioned on the structure, providing a segmented contact electrode on the cap layer, wherein the segmented electrode further comprises a first contact electrode and a second contact electrode separated from each other by a surface-sensitive gap region, wherein a distance between the first electrode and the second electrode is more than 2 microns, but less than 150 microns, bringing a sample into the surface sensitive gap region, and detecting laser optical output by changes input power, output spectral characteristics output signal autocorrelation function depending upon the presence of chemical or biological films within the surface sensitive gap region correlating the changes in output power, output spectral characteristic or output signal autocorrelation function to the absence or presence of the chemical or biological film further comprising providing gap electrode within the gap region between the contact electrodes and pulsing the gap electrodes.

2. The method of claim 1, further comprising providing two gap electrodes with the gap region, where applied potential of one of the gap electrodes is cycled from a starting point of −0.8 V to a maximum potential of +0.8 V within a time frame and monitoring output of the diode laser just after increasing the potential.

3. The method of claim 2, further comprising subsequently step changing the applied potential of the gap electrodes from +0.8 V to +0.2 V and thereafter which time monitoring an output signal of the diode laser.

4. A method for chemical and biological sensing comprising providing a diode laser with a layered semiconducting structure, and a cap layer positioned on the structure, providing a segmented contact electrode on the cap layer, wherein the segmented electrode further comprises a first contact electrode and a second contact electrode separated from each other by a surface-sensitive gap region, wherein a distance between the first electrode and the second electrode is more than 2 microns, but less than 150 microns, bringing a sample into the surface sensitive gap region, and detecting laser optical output by changes in output power, output spectral characteristics output signal autocorrelation function depending upon the presence of chemical or biological films within the surface sensitive gap region correlating the changes in output, power output spectral characteristic or output signal autocorrelation function to the absence or presence of the chemical or biological film further comprising providing a voltage between the gap electrode and contact electrodes of about +2 V or −2 V, for organic solutions.

5. The method of claim 4, further comprising applying the potential according to a range of waveforms (step, triangular or sinusoid) and monitoring laser output as a change in at least one of output power, output spectral characteristics and output signal autocorrelation function.

* * * * *